US008945488B2

(12) United States Patent
Bowe et al.

(10) Patent No.: US 8,945,488 B2
(45) Date of Patent: Feb. 3, 2015

(54) GAS-TO-LIQUID TECHNOLOGY

(75) Inventors: Michael Joseph Bowe, Preston (GB);
Robert Peat, Longcot (GB); David James West, Ducklington (GB); Philip Hawker, County Kerry (IE)

(73) Assignee: CompactGTL Limited (GB)

( * ) Notice: Subject to any disclaimer, the term of this patent is extended or adjusted under 35 U.S.C. 154(b) by 0 days.

(21) Appl. No.: 13/638,009

(22) PCT Filed: Apr. 27, 2011

(86) PCT No.: PCT/GB2011/050831
§ 371 (c)(1),
(2), (4) Date: Sep. 28, 2012

(87) PCT Pub. No.: WO2011/135357
PCT Pub. Date: Nov. 3, 2011

(65) Prior Publication Data
US 2013/0041049 A1 Feb. 14, 2013

(30) Foreign Application Priority Data

Apr. 30, 2010 (GB) .................................. 1007196.7

(51) Int. Cl.
*C10G 2/00* (2006.01)
*C01B 3/34* (2006.01)
*C10L 3/10* (2006.01)

(52) U.S. Cl.
CPC ... *C01B 3/34* (2013.01); *C10G 2/32* (2013.01);
*C10L 3/10* (2013.01); *C01B 2203/0233*
(2013.01); *C01B 2203/0244* (2013.01);
(Continued)

(58) Field of Classification Search
CPC .... C10G 2/34; C10L 3/107; B01J 2208/0628;
B01J 2219/00002
See application file for complete search history.

(56) References Cited

U.S. PATENT DOCUMENTS 2,472,219 A * 6/1949 Lyons ........................... 518/704
4,932,213 A   6/1990 Summers et al.
(Continued)

FOREIGN PATENT DOCUMENTS

CA    1316547 C    4/1993
EP    1 808 408 A2  7/2007
(Continued)

OTHER PUBLICATIONS

International Search Report and Written Opinion for PCT/GB2011/050831 dated Jul. 29, 2011.
(Continued)

*Primary Examiner* — Lessanework Seifu
(74) *Attorney, Agent, or Firm* — McDermott Will & Emery LLP

(57) ABSTRACT

A gas-to-liquids process and plant for treating natural gas, in which the natural gas is subjected to expansion through a flow restrictor so as to undergo cooling through the Joule Thomson effect, enables liquids to be separated from the gas stream. The natural gas may be cooled before it reaches the flow restrictor by heat exchange with fluid that has passed through the flow restrictor. This decreases the proportion of longer-chain hydrocarbons in the natural gas, which may simplify subsequent processing, and may enable the size of the plant to be decreased.

7 Claims, 1 Drawing Sheet

(52) U.S. Cl.
CPC ... *C01B2203/025* (2013.01); *C01B 2203/0405* (2013.01); *C01B 2203/043* (2013.01); *C01B 2203/062* (2013.01); *C01B 2203/0811* (2013.01); *C01B 2203/0822* (2013.01); *C01B 2203/0827* (2013.01); *C01B 2203/0894* (2013.01); *C01B 2203/1064* (2013.01); *C01B 2203/1241* (2013.01); *C10G 2300/1025* (2013.01)
USPC .......... 422/625; 422/608; 422/609; 422/620; 422/621; 422/630; 518/702; 518/704

(56) References Cited

U.S. PATENT DOCUMENTS

| | | | | |
|---|---|---|---|---|
| 5,771,712 | A | * | 6/1998 | Campbell et al. ............... 62/621 |
| 6,743,829 | B2 | * | 6/2004 | Fischer-Calderon et al. . 518/700 |
| 7,437,889 | B2 | * | 10/2008 | Roberts et al. .................. 62/619 |
| 2003/0136146 | A1 | | 7/2003 | Fischer-Calderon et al. |
| 2006/0213223 | A1 | | 9/2006 | Wilding et al. |
| 2008/0173363 | A1 | | 7/2008 | Betting |
| 2008/0210596 | A1 | * | 9/2008 | Litt et al. ....................... 208/20 |

FOREIGN PATENT DOCUMENTS

| | | | |
|---|---|---|---|
| EP | 1867940 | A2 | 12/2007 |
| GB | 1011453 | A | 12/1965 |
| JP | 54103797 | | 2/1978 |
| WO | WO 01/02089 | A1 | 1/2001 |
| WO | WO 01/51194 | A1 | 7/2001 |
| WO | WO 03/006149 | A1 | 1/2003 |
| WO | WO 2004/050799 | A1 | 6/2004 |
| WO | WO 2007/018677 | * | 2/2007 |
| WO | WO 2008/005518 | A2 | 1/2008 |

OTHER PUBLICATIONS

International Search Report for GB 1007196.7 dated Aug. 23, 2010.

* cited by examiner

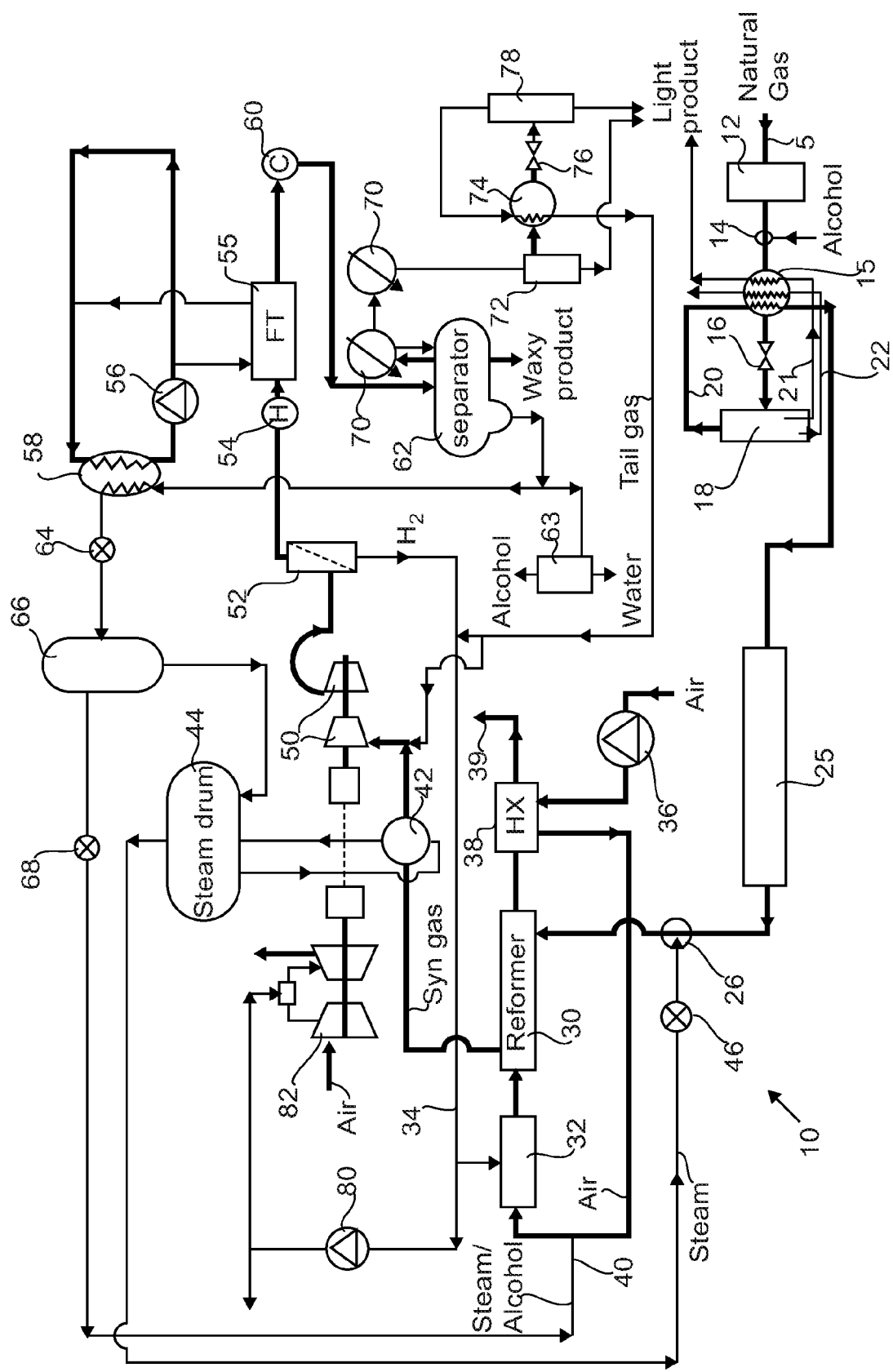

GAS-TO-LIQUID TECHNOLOGY

The present invention relates to a plant and a process for treating natural gas to produce a liquid product.

It is well known that most oil wells also produce natural gas. At many oil wells natural gas is produced in relatively small quantities along with the oil. When the quantities of this associated gas are sufficiently large or the well is close to pre-existing gas transportation infrastructure, the gas can be transported to an off-site processing facility. When oil production takes place in more remote places it is difficult to introduce the associated gas into existing gas transportation infrastructure. In the absence of such infrastructure, the associated gas has typically been disposed of by flaring or re-injection. However, flaring the gas is no longer an environmentally acceptable approach, while re-injection can have a negative impact on the quality of the oil production from the field.

Gas-to-liquids technology can be used to convert the natural gas into liquid hydrocarbons and may follow a two-stage approach to hydrocarbon liquid production comprising syngas generation, followed by Fischer-Tropsch synthesis. In general, syngas (a mixture of hydrogen and carbon monoxide) may be generated by one or more of partial oxidation, auto-thermal reforming, or steam methane reforming. Where steam methane reforming is used, the reaction is endothermic and so requires heat. The syngas is then subjected to Fischer-Tropsch synthesis. For performing Fischer-Tropsch synthesis the optimum ratio of hydrogen to carbon monoxide is about 2:1, and steam reforming has a benefit of providing more than sufficient hydrogen for this purpose.

Such a process is described for example in WO 01/51194 (AEA Technology) and WO 03/006149 (Accentus plc). Natural gas is primarily methane, but also contains small proportions of longer-chain hydrocarbons. In each case the natural gas is first subjected to a pre-reforming step in which the longer-chain hydrocarbons are converted to methane by reaction with steam, for example over a nickel catalyst at 400° C. As regards the Fischer-Tropsch process, as described in WO 2004/050799 (GTL Microsystems AG), a suitable catalyst uses small particles of cobalt on a ceramic support, but this catalyst can suffer a deleterious reaction in the presence of water vapour. To ensure this does not occur the reactor is operated so as to ensure the Fischer-Tropsch conversion is no more than 70%, and then the resulting gases are subjected to a second Fischer-Tropsch stage. Although this provides a satisfactory way of converting natural gas to a longer-chain hydrocarbon product, it would be desirable to provide an alternative plant and process.

According to the present invention there is provided a gas-to-liquids plant for treating natural gas, wherein the natural gas is subjected to expansion through a flow restrictor so as to undergo cooling through the Joule Thomson effect, with separation of resulting liquids.

The present invention also provides a process for treating natural gas in this way. The process of the invention relates to a chemical process for converting natural gas (primarily methane) to longer chain hydrocarbons.

Ideally the expansion takes place without significant transfer of heat from the surroundings, the natural gas expanding into a lower pressure state. The flow restrictor may be a throttle valve, or alternatively may be an inlet nozzle of a vortex tube separator, or a turbo expander, or a Twister™ separator device. A vortex tube, or Ranque-Hilsch tube, splits the gas into a hot gas stream and a cold gas stream. The hot gas stream may be utilised elsewhere within the plant. However, as a result of the division into two streams, only a proportion of the gases are cooled. The expansion can cool the natural gas to below 0° C., more particularly below −10° C. for example below −15° C., with the consequence that longer-chain hydrocarbons condense from the vapour state into the liquid state, and can be separated from the remaining natural gas. The degree of cooling is selected to ensure that the output stream is at a pressure sufficient to drive gas through the process. Whilst the temperature can be dropped further in order to increase the recovery of higher hydrocarbons, this ceases to be advantageous when the cost of the increased compression requirements to re-pressurize the gas exceed the value of the additional longer chain hydrocarbons recovered. Preferably the natural gas stream is fed into the flow restrictor through a heat exchanger in which it is cooled by contact with at least one fluid that has been cooled by passage through the flow restrictor, so that the natural gas is below ambient temperature when it reaches the flow restrictor.

A benefit of this process is that the proportion of longer-chain hydrocarbons in the remaining natural gas is considerably reduced. It may therefore be practicable to then subject the natural gas to reforming without the need for a separate pre-reformer. A further benefit is that the quantity of hydrocarbons subjected to the subsequent chemical processes is reduced, which may reduce the size and hence the cost of the remainder of the plant.

A potential problem in such a cooling process is the risk of formation of methane-containing hydrates, although this may not be an issue with a Twister device as the residence time may be sufficiently short to prevent formation of hydrate crystals. To address this issue, oxygenates such as methanol or ethanol may be introduced into the natural gas stream upstream of the flow restrictor. These prevent the formation of hydrates. In the context of a gas-to-liquid plant, such oxygenates are produced during the Fischer-Tropsch synthesis, and can be extracted from the resulting aqueous phase by steam stripping. These oxygenates hence allow the gas stream to be cooled to a lower temperature. The natural gas is then converted to synthesis gas either by steam methane reforming, partial oxidation or auto-thermal reforming. In the case of steam methane reforming, the requisite heat may be provided by catalytic combustion within adjacent channels within an integrated reforming/combustion reactor, or by hot exhaust gases from a separate combustion reactor. The resulting synthesis gas contains more hydrogen than is required for Fischer-Tropsch synthesis, and at least some excess hydrogen may be separated from the synthesis gas by a membrane separator, and supplied to a fuel header. If a membrane is not used for separation, separation can be performed by pressure swing absorption. The fuel header may supply the fuel for the combustion process that provides the heat for the steam methane reforming reaction, or may provide fuel for preheating an air supply for such a combustion process.

The synthesis gas may then be subjected to a Fischer-Tropsch synthesis reaction to convert the synthesis gas into longer chain hydrocarbons. This may be a single stage process or a two-stage process. After separating liquid hydrocarbon product and an aqueous phase, for example in a tubular heat exchanger followed by separation by density differences in a vessel, there is a resulting tail gas. The tail gas contains hydrogen, carbon monoxide, carbon dioxide and methane. Some of the tail gas is preferably fed into the synthesis gas stream, preferably upstream of the membrane separator. At least some of the tail gas is fed into the fuel header.

At least some of the aqueous phase may be boiled to produce a steam and oxygenate-containing vapour, which is fed into the combustion gas mixture. For example it may be fed into a stream of combustion air supplied to combustion channels or to a combustion reactor.

It will be appreciated that the steam/methane reforming process produces two hot out-flowing streams: a synthesis gas stream typically at above 800° C., and an exhaust gases stream which may be at a similar temperature (if an integrated combustion/reforming reactor is used) or which may be at a somewhat lower temperature (if a separate combustion reactor is used). Preferably these hot streams are used to provide thermal energy to gases being supplied to the reforming process. For example the hot synthesis gas may be used to provide the steam required for reforming, while the exhaust gases may be used to preheat combustion air.

In a further aspect of the present invention there is provided a gas-to-liquid process, and a plant to perform the process, wherein the process utilises a combustion step using a stream of air, and wherein the process produces excess hydrogen, wherein excess hydrogen is separated using a membrane or using pressure swing absorption, and is used to preheat the combustion air stream. The preheating of the air stream may utilise a catalytic combustion process. For example the hydrogen may be separated from a synthesis gas or from a tail gas of a Fischer-Tropsch synthesis reaction.

In yet a further aspect the present invention provides a gas-to-liquid process, and a plant to perform the process, wherein the process utilises a combustion step, and where the process performs Fischer-Tropsch synthesis, wherein heat from the Fischer-Tropsch synthesis is used to generate steam, and the steam is introduced into a gas stream supplied to the combustion step. The steam that is supplied to the combustion step may include oxygenates that are produced as a byproduct of the Fischer-Tropsch synthesis.

The invention will now be further and more particularly described, by way of example only, and with reference to the accompanying drawing which shows a schematic flow diagram of a gas-to-liquid plant and associated equipment.

The invention relates to a chemical process for converting natural gas (primarily methane) to longer chain hydrocarbons. It is suitable for treating associated gas, which is natural gas that is produced along with crude oil, and is then separated from the crude oil. The first stage of the chemical process involves the formation of synthesis gas, for example by steam reforming, by a reaction of the type:

$$H_2O + CH_4 \rightarrow CO + 3H_2 \quad (1)$$

This reaction is endothermic, and may be catalysed by a rhodium or platinum/rhodium catalyst in a first gas flow channel. The heat required to cause this reaction may be provided by catalytic combustion of a gas such as methane or hydrogen, which is exothermic, in an adjacent channel, or by heat exchange with exhaust gases from a separate combustion reactor. The combustion may be catalysed by a palladium catalyst in an adjacent second gas flow channel in a compact catalytic reactor. In both cases the catalyst may be on a stabilised-alumina support which forms a coating typically less than 100 μm thick on a metallic substrate. Alternatively, the catalyst may be applied to the walls of the flow channels or may be provided as pellets within the flow channel. The heat generated by the combustion would be conducted through the metal sheet separating the adjacent channels.

The gas mixture produced by the steam/methane reforming is then used to perform a Fischer-Tropsch synthesis to generate a longer chain hydrocarbon, that is to say:

$$nCO + 2nH_2 \rightarrow (CH_2)_n + nH_2O \quad (2)$$

which is an exothermic reaction, occurring at an elevated temperature, typically between 190° C. and 280° C., for example 230° C., and an elevated pressure typically between 1.8 MPa and 2.6 MPa (absolute values), for example 2.5 MPa, in the presence of a catalyst such as iron, cobalt or fused magnetite, with a potassium promoter. Whilst Fe based catalysts can be used, metallic Co promoted with precious metals such as Pd, Pt, Ru or Re doped to 1 wt % are preferred when operating at lower temperatures as they have enhanced stability to oxidation. The active metals are impregnated to 10-40 wt % into refractory support materials such as $TiO_2$, $Al_2O_3$ or $SiO_2$ which may be doped with rare earth and transition metal oxides to improve their hydrothermal stability.

1. Pre-Treatment

Referring to FIG. 1, there is shown a gas-to-liquid plant 10 of the invention. A natural gas feed 5 consists primarily of methane, but with small proportions of other gaseous hydrocarbons, hydrocarbon vapours, and water vapour. The gas feed 5 may for example be at a pressure of 4.0 MPa (40 atmospheres) and 35° C., following sea water cooling from an initial temperature of 90° C., and may constitute associated gas from a well producing crude oil. The natural gas feed 5 is first passed through a coalescer 12 which removes any droplets. A small quantity of oxygenates (primarily ethanol and methanol, and marked "alcohol") is then sprayed into the gas feed 5 at an injector 14, and the gas feed 5 is then passed through a heat exchanger 15 to cool it, and then through a throttle valve 16 through which it expands into a lower pressure region (typically at about 1 MPa) adiabatically, with no significant heat input from the surroundings. Consequently, in accordance with the Joule Thomson effect, the natural gas is considerably cooled, for example to −18° C. The resulting cooled stream is then fed into a phase separator 18, so producing a gas phase 20, a liquid hydrocarbon phase 21, and an aqueous phase 22 (containing the oxygenates). The use of the oxygenates ensures that methane-containing hydrates are not produced. All three of these fluids streams are passed through the heat exchanger 15 so as to cool the in-flowing gas feed 5.

The liquid hydrocarbon phase 21 constitutes part of the product output stream of liquid hydrocarbon from the plant 10.

The gas phase 20 is then subjected to pretreatment 25, which may comprise one or more of the following: changing its pressure; changing its temperature; and removing impurities such as sulphur. It is then mixed with steam in a mixer 26.

2. Making Synthesis Gas

The gas/steam mixture, preferably at a temperature of about 450° C., is then fed into a catalytic steam/methane reformer 30. The reformer 30 consists of a compact catalytic reactor formed from a stack of plates defining two sets of channels arranged alternately. One set of channels are for the reforming reaction, and contain a reforming catalyst on removable corrugated metal foil supports, while the other set of channels are for the provision of heat.

In this example the heat is provided using a separate burner 32, the exhaust gases from the burner 32 at about 850° C. being passed through the reformer 30 in counter-current to the flow of the steam/methane mixture. The reaction channels of the reformer 30 may contain a nickel catalyst in an initial part of the channel, of length between 100 and 200 mm, for example 150 mm, out of a total reaction channel length of 600 mm. In the first part of the channel, where the nickel catalyst is present, pre-reforming takes place, so any higher hydrocarbons will react with steam to produce methane. The remainder of the length of the reaction channels contains a reformer catalyst, for example a platinum/rhodium catalyst, where the steam and methane react to form carbon monoxide and hydrogen.

The heat for the steam/methane reforming reaction in the reformer 30 is provided by combustion of a fuel gas from a fuel header 34 in a stream of combustion air. In this example the fuel gas is primarily hydrogen. The combustion air is provided by a blower 36 and is preheated in a heat exchanger 38, taking heat from the hot exhaust gases from the combustion after they have passed through the reformer 30. In addition a mixture of steam and alcohol vapour 40 is introduced into the combustion air upstream of the burner 32. After passing through the heat exchanger 38 the exhaust gases may be vented through a stack 39.

A mixture of carbon monoxide and hydrogen at above 800° C. emerges from the reformer 30, and is quenched to below 400° C. by passing it through a steam-raising heat exchanger 42 in the form of a thermosiphon. The heat exchanger 42 is a tube and shell heat exchanger, the hot gases passing through the tubes, and with inlet and outlet ducts communicating with the shell at the top and bottom, and communicating with a steam drum 44. The steam drum 44 is about half full of water, and so water circulates through natural convection between the heat exchanger 42 and the steam drum 44. The resulting steam from the steam drum 44 is supplied to the mixer 26 through a control valve 46.

The gas mixture, which is a form of synthesis gas, may be subjected to further cooling (not shown). It is then subjected to compression using two successive compressors 50, preferably with cooling and liquid-separation stages (not shown) after each compressor 50. The compressors 50 raise the pressure to about 2.5 MPa (25 atm).

It will be appreciated from equation (1) above that the ratio of hydrogen to CO produced in this way is about 3:1, whereas the stoichiometric requirement is about 2:1, as is evident from equation (2). The high-pressure synthesis gas is therefore passed by a hydrogen-permeable membrane 52 to remove excess hydrogen. This hydrogen is supplied to the fuel header 34, and is the principal fuel gas.

3. Fischer-Tropsch Synthesis And Product Treatment

The stream of high pressure carbon monoxide and hydrogen is then heated to about 200° C. in a heat exchanger 54, and then fed to a catalytic Fischer-Tropsch reactor 55, this again being a compact catalytic reactor formed from a stack of plates as described above; the reactant mixture flows through one set of channels, while a coolant flows through the other set. The coolant is circulated by a pump 56 and through a heat exchanger 58. The Fischer-Tropsch reaction takes place at about 210° C., and the coolant is circulated at such a rate that the temperature varies by less than 10 K on passage through the reactor 55.

The reaction products from the Fischer-Tropsch synthesis, predominantly water and hydrocarbons such as paraffins, are cooled to about 70° C. to condense the liquids by passage through a heat exchanger 60 and fed to a separating chamber 62 in which the three phases water, hydrocarbons and tail gases separate. The aqueous phase contains water with about 1-2% oxygenates such as ethanol and methanol which are formed by the Fischer-Tropsch synthesis. Most of the aqueous phase from the separating chamber 62 is treated by steam stripping 63 to separate the oxygenates (marked "alcohol") to leave clean water that may be discharged to waste. The separated oxygenates, which are at an oxygenate concentration of about 80%, are injected into the injector 14 upstream of the throttle valve 16 as described above. The remainder of the aqueous phase is fed as process water through the heat exchanger 58, and hence through a pressure-drop valve 64 into a stripper tank 66. In the stripper tank 66 the aqueous phase boils, typically at a pressure of about 1.0 MPa (10 atm), the liquid phase being fed from the bottom of the stripper tank 66 into the steam drum 44, while the vapour phase, which contains steam and the bulk of the oxygenates, provides the stream 40 that is introduced into the combustion air through a control valve 68.

The hydrocarbon phase from the separating chamber 62 is the longer-chain hydrocarbon product. The vapour and gas phase from the separating chamber 62 is fed through two successive cooling heat exchangers 70, the second of which cools the vapours to ambient temperature. Any liquids that condense on passage through the first heat exchanger 70 are fed back into the separating chamber 62. The output from the second heat exchanger 70 is fed into a phase separating chamber 72, where the water and light hydrocarbon product liquid separate.

The remaining vapour phase, which is at the same pressure as the Fischer-Tropsch reactor 55, is then passed through a heat exchanger 74 to a throttle valve 76 followed by a phase separating vessel 78. As the gas passes through the throttle valve 76 it expands into a lower pressure region adiabatically, with no significant heat input from the surroundings. Consequently, in accordance with the Joule Thomson effect, the gas is cooled considerably. The liquids that emerge from the phase separating pressure 78 contain water and light hydrocarbon product. The gases that emerge from the phase separating vessel 78, which are the tail gases from the Fischer-Tropsch process, are passed back through the heat exchanger 74 to cool the in-flowing gases and, optionally, through a hydrogen permeable membrane (not shown). Part of the tail gas may be fed back into the synthesis gas stream upstream of the first compressor 50. At least part of the tail gas is fed into the fuel header 34, to ensure that there is no excessive build-up of methane in the Fischer-Tropsch reactor 55.

4. Energy Transfer And Process Review

The fuel header 34 not only provides the fuel for the burner 32, but also supplies fuel via a fuel compressor 80 to a gas turbine 82. Indeed compressed fuel gas may also be supplied to other equipment (not shown) that does not form part of the plant 10. The gas turbine 82 may be arranged to provide electrical power for operating the plant 10. As indicated by a broken line in the figure, in this example the electrical power generated by the gas turbine 82 is used to power the compressors 50. Alternatively the gas turbine 82 may be coupled directly to drive the compressors 50.

It will be appreciated that in the above-described process the heat produced by the Fischer-Tropsch reaction is used in boiling steam and alcohol in the stripper tank 66, and so is transferred to the combustion channels by the feed 40. The remaining heat required for reforming is provided by the fuel gas from the fuel header 34 undergoing combustion in the burner 32. This may be a duct burner, in which there are several nozzles through which fuel gas is fed into a stream of combustion air, so it burns with a flame. Alternatively the burner 32 may be a catalytic flame-less combustion unit. As previously mentioned, the resulting hot exhaust gas supplies heat to the reformer 30, and is then used to preheat combustion air in the heat exchanger 38.

In a modification to the above-described process the combustion air may be additionally pre-heated by introducing hydrogen into the combustion air, and passing it through a honeycomb structure of an aluminium-containing ferritic steel such as Fecralloy, with an oxidised surface, which has been found to be a catalytic to hydrogen combustion. Alternatively the preheating may be performed using a duct burner in which a fuel such as hydrogen is burnt. The final heating of the combustion air to the desired temperature in the vicinity of 800° C. may then be achieved using a duct burner 32 to which a combustible gas stream is provided, such as the tail gas from the Fischer-Tropsch process, or as described above using a burner 32 which is a catalytic flame-less combustion unit.

In a further modification, the combustion air is preheated either by passage through a duct burner provided with a suitable fuel, or by introducing hydrogen into the combustion air, and passing it through a honeycomb structure of aluminium-containing ferritic steel as described above, so that hydrogen undergoes catalytic combustion. The hot combustion air is then fed into an integrated combustion/reforming reactor, and a fuel such as methane or tail gas is introduced and subjected to catalytic combustion in the heat-providing channels of the reactor through which the hot combustion air flows. In this modification the catalytic combustion may, for example, take place over a palladium/platinum catalyst within the heat-providing channels within the reforming reactor 30. In this case the combustion gas path is preferably co-current relative to the reformer gas path. The catalyst may include gamma-alumina as a support, coated with a palladium/platinum 3:1 mixture, which is an effective catalyst over a wide temperature range. The combustible gas mixture may be supplied in stages along the reactor 30 to ensure combustion occurs throughout the length of the combustion channels.

The invention claimed is:

1. A gas-to-liquids plant for treating natural gas, the plant comprising:
   a flow restrictor configured to subject the gas to expansion so as to undergo cooling through the Joule Thomson effect, and a phase separator configured to separate resulting longer-chain hydrocarbon liquid from remaining natural gas;
   a catalytic reformer comprising channels for a reforming reaction configured to process the remaining natural gas to form a synthesis gas, and further comprising channels for the provision of heat provided by a combustion process;
   a Fischer-Tropsch reactor to which the synthesis gas is provided;
   a separating chamber to separate hydrocarbon product and aqueous phase from the output of the Fischer-Tropsch reactor;
   a steam stripper configured to separate oxygenates from part of the aqueous phase;
   an injector configured to introduce the oxygenates into the natural gas stream upstream of the flow restrictor;
   a heat exchanger and a tank configured to extract at least some of the heat output by the Fischer-Tropsch reactor, and thereby to cause part of the aqueous phase to boil and so generate a vapour phase comprising steam and oxygenates; and,
   a duct configured to introduce the vapour phase into an air stream for the combustion process.

2. A plant as claimed in claim 1 comprising a heat exchanger arranged for heat transfer between the natural gas before it reaches the flow restrictor, and at least one fluid that has been cooled by passage through the flow restrictor.

3. A plant as claimed in claim 1 wherein the catalytic reformer forms a synthesis gas containing excess hydrogen, and wherein the plant further comprises a separator to remove hydrogen from the synthesis gas.

4. A plant as claimed in claim 3 including a fuel header to which separated hydrogen is supplied.

5. A plant as claimed in claim 4 wherein the combustion process is, at least in part, combustion of fuel from the fuel header.

6. A plant as claimed in claim 4 comprising a phase separator to separate tail gas from the output from the Fischer-Tropsch reactor, wherein some of the tail gas is recirculated into the synthesis gas stream, and some of the tail gas is fed into the fuel header.

7. A plant as claimed in claim 5 further comprising a preheater, to which the air stream for combustion is provided, the air stream being mixed with hydrogen from the removed excess hydrogen, the preheater comprising a catalytic structure including an aluminium-containing ferritic steel without any catalytic coating, configured so that the hydrogen removed from the synthesis gas undergoes catalytic combustion at the surface of the steel.

\* \* \* \* \*